United States Patent
Draper

(10) Patent No.: US 9,764,095 B2
(45) Date of Patent: Sep. 19, 2017

(54) PEN-TYPE DRUG INJECTION DEVICE AND OPTICAL DOSE VALUE DECODING SYSTEM WITH ADDITIONAL SENSOR TO DISTINGUISH BETWEEN DOSE DIALLING AND DOSE DELIVERY MODE

(71) Applicant: Sanofi-Aventis Deutschland GmbH, Frankfurt am Main (DE)

(72) Inventor: Paul Richard Draper, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 93 days.

(21) Appl. No.: 14/760,691

(22) PCT Filed: Jan. 13, 2014

(86) PCT No.: PCT/EP2014/050467
§ 371 (c)(1),
(2) Date: Jul. 13, 2015

(87) PCT Pub. No.: WO2014/111340
PCT Pub. Date: Jul. 24, 2014

(65) Prior Publication Data
US 2016/0015902 A1    Jan. 21, 2016

(30) Foreign Application Priority Data

Jan. 15, 2013 (DE) ................................. 131 51 370

(51) Int. Cl.
*G01D 5/34* (2006.01)
*A61M 5/315* (2006.01)
(Continued)

(52) U.S. Cl.
CPC .......... *A61M 5/31525* (2013.01); *A61M 5/20* (2013.01); *G06K 7/10881* (2013.01);
(Continued)

(58) Field of Classification Search
CPC .................................................. A61M 5/31525
See application file for complete search history.

(56) References Cited

U.S. PATENT DOCUMENTS 4,919,650 A  *  4/1990  Feingold ............. A61M 5/1452
128/DIG. 13
2005/0274915 A1   12/2005  Holcomb et al.
(Continued)

FOREIGN PATENT DOCUMENTS

WO   2010098927 A1   9/2010
WO   2010139640 A1   12/2010
(Continued)

*Primary Examiner* — Tony Ko
(74) *Attorney, Agent, or Firm* — McDonnell Boehnen Hulbert & Berghoff LLP

(57) ABSTRACT

An optical decoding system comprising: a first optical sensor configured to be directed at a first rotatable component of a drug delivery device; a second optical sensor configured to be directed at a second rotatable component of a drug delivery device; and a processor configured to: receive signals from the first optical sensor, wherein the signals from the first optical sensor represent encoded dosage values present on the first rotatable component; receive signals from the second optical sensor, wherein the signals from the second optical sensor represent whether the second rotatable component is rotating or not; and to determine from the received signals whether the drug delivery device is in a drug dose dialing mode or a drug dose delivery mode.

9 Claims, 6 Drawing Sheets

(51) Int. Cl.
   *A61M 5/20* (2006.01)
   *G06K 7/10* (2006.01)
   *A61M 5/24* (2006.01)
   *G01D 5/347* (2006.01)

(52) U.S. Cl.
   CPC ........... *A61M 5/24* (2013.01); *A61M 5/31551* (2013.01); *A61M 2205/3306* (2013.01); *A61M 2205/8212* (2013.01); *G01D 5/3473* (2013.01); *G01D 5/34792* (2013.01)

(56) References Cited

U.S. PATENT DOCUMENTS

2006/0224123 A1    10/2006    Friedli et al.
2011/0270214 A1    11/2011    Jorgensen et al.

FOREIGN PATENT DOCUMENTS

| WO | 2011117212 A1 | 9/2011 |
| WO | 2012/022771 A2 | 2/2012 |
| WO | 2012140097 A2 | 10/2012 |
| WO | 2013004844 A1 | 1/2013 |

\* cited by examiner

PEN-TYPE DRUG INJECTION DEVICE AND OPTICAL DOSE VALUE DECODING SYSTEM WITH ADDITIONAL SENSOR TO DISTINGUISH BETWEEN DOSE DIALLING AND DOSE DELIVERY MODE

CROSS REFERENCE TO RELATED APPLICATIONS

The present application is a U.S. National Phase Application pursuant to 35 U.S.C. §371 of International Application No. PCT/EP2014/050467 filed Jan. 13, 2014, which claims priority to European Patent Application No. 13151370.7 filed Jan. 15, 2013. The entire disclosure contents of these applications are herewith incorporated by reference into the present application.

FIELD OF INVENTION

The present invention relates to an optical decoding system for a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to optical decoding systems for injectors, for example hand-held injectors, especially pen-type injectors, that is to injectors of the kind that provide for administration by injection of medicinal products from a multidose cartridge.

A user undertaking self-administration of insulin will commonly need to administer between 1 and 80 International Units. A user is also required to record their dosage history. The dosage history is an important factor in calculating future doses.

SUMMARY

A first aspect of the invention provides an optical decoding system comprising:

a first optical sensor configured to be directed at a first rotatable component of a drug delivery device;

a second optical sensor configured to be directed at a second rotatable component of a drug delivery device; and a processor configured to receive signals from the first and second optical sensors and to determine a mode of operation of the drug delivery device from the received signals.

The current mode of operation of the drug delivery device can then be communicated to a user of the device. The user does not have to determine the mode themselves.

Being able to determine the mode of operation of the drug delivery device is advantageous, as the dose of medicament which has been delivered can be determined. It is important to accurately record the dose of medicament which has actually been delivered in order to accurately assess the effect of the medicament on the user's health and for the calculation of future medicament doses.

The first rotatable component may be arranged to rotate and translate relative to the first optical sensor when the drug delivery device is in a first mode and in a second mode, while the second rotatable component may be arranged to rotate and translate relative to the second optical sensor when the drug delivery device is in the first mode and only to translate when the drug delivery device is in the second mode. The difference in movement between the first and second rotatable components allows the operational mode of the device to be determined.

The first mode may be a drug dose dialing mode and the second mode may be a drug dose delivery mode.

The processor may be further configured to determine a drug dose that has been delivered and to cause a record of the delivered dose to be stored in a memory. The processor may be configured to determine the drug dose that has been delivered using signals received from the first optical sensor. This allows the delivered dose to be calculated automatically and accurately. It is often necessary for a user of such a drug delivery device to adjust the medicament dose based at least in part on their previous doses. It is therefore advantageous to accurately and automatically record all dispensed doses.

The optical decoding system may further comprise a display device and the processor may be configured to cause the display device to display an indication of the drug dose that has been delivered.

The optical decoding system may further comprise one or more LEDs configured to illuminate portions of the first and/or second rotatable components. The reliability and sensitivity of images captured by the first and/or second optical sensors may be improved if the rotatable components are illuminated.

The optical decoding system may further comprise a switch and a change in the state of the switch may be configured to cause the first and second optical sensors to be activated. The drug delivery device and switch may be configured to be arranged such that the state of the switch changes when the drug delivery device moves from a zero unit drug dose arrangement to a single unit drug dose arrangement. Activating the first and second sensors only when a change in the state of a switch is detected results in power savings compared to powering the sensors whenever the drug delivery device is on.

A second aspect of the invention provides a drug delivery device comprising a housing retaining the optical decoding system of the first aspect of the invention. The drug delivery device may comprise the first rotatable component and the second rotatable component. Integrating the optical decoding system with the drug delivery device increases the utility of that device.

In a third aspect of the invention, the optical decoding system of the first aspect may be part of a supplementary device configured to be attached to the drug delivery device. Implementing the optical decoding system in a supplementary device allows the optical decoding system to be applied to devices without an electronic monitoring capability, or with a less sophisticated monitoring capability.

A fourth aspect of the invention provides a method of determining a mode of operation of a drug delivery device comprising:

receiving a signal from a first optical sensor directed at a first rotatable component of the drug delivery device;

receiving a signal from a second optical sensor directed at a second rotatable component of the drug delivery device; and determining that the drug delivery device is in a first mode of operation if the second rotatable component is rotating when the first rotatable component is rotating or determining that the drug delivery device is in a second mode of operation if the second rotatable component is not rotating when the first rotatable component is rotating.

Being able to determine the mode of operation of the drug delivery device is advantageous, as the dose of medicament which has been delivered can be determined. It is important to accurately record the dose of medicament which has actually been delivered in order to accurately assess the effect of the medicament on the user's health and for the calculation of future medicament doses. The difference in movement between the first and second rotatable components allows the operational mode of the device to be determined.

The first mode of operation may be a drug dose dialing mode and the second mode of operation may be a drug dose delivery mode.

BRIEF DESCRIPTION OF THE DRAWINGS

Embodiments will now be described, by way of example only, with reference to the accompanying drawings, in which:

FIG. 1b shows an internal view of the drug delivery device of FIG. 1a;

DETAILED DESCRIPTION

Figure 1A:
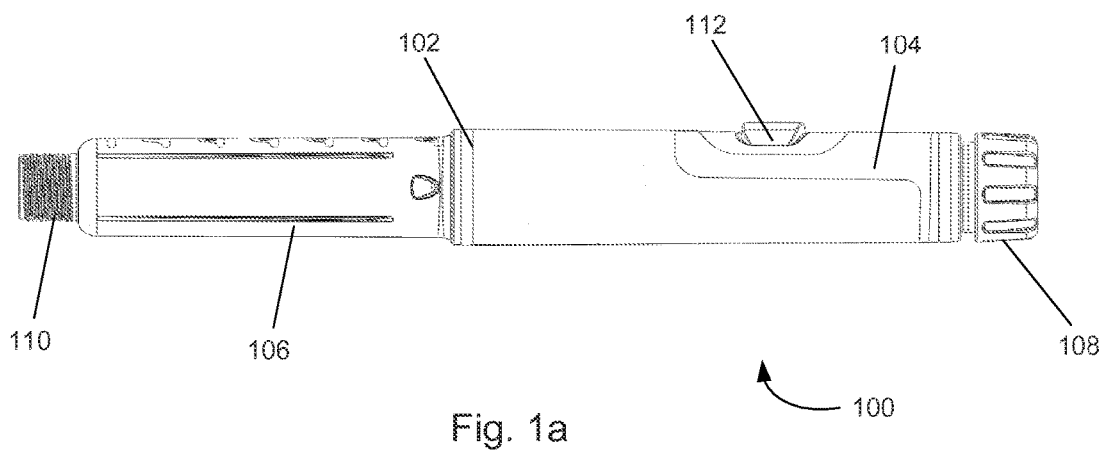
FIG. 1a shows an external view of a drug delivery device suitable for implementing the present invention.
Figure 1B:
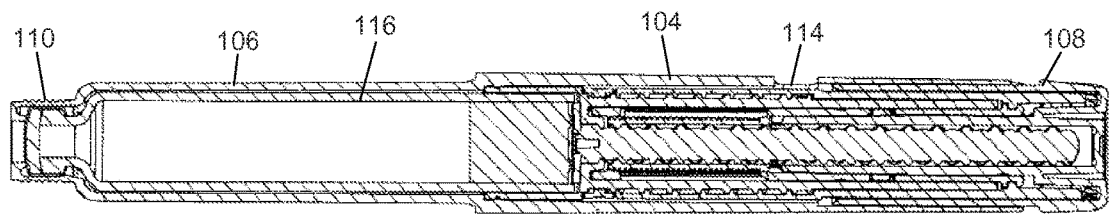

Referring firstly to FIGS. 1a and 1b, an external view and an internal view of a drug delivery device 100 according to embodiments of the invention are shown. The device 100 shown in FIGS. 1a and 1b is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display window 112 is located on the first housing part 104. A display may be disposed underneath the display window 112. The display may be an LCD display, a segmented display or any other suitable type of display. The display window 112 may cover a recess 114 in the first housing portion 104. As well as a display, a number of electronic components, described in greater detail with reference to FIG. 2, may be disposed underneath the display window 112.

The first housing part 104 contains a drug dose setting and delivery mechanism. The second housing part 106 contains a drug cartridge 116. The drug contained in the drug cartridge 116 may be a medicament of any kind and may preferably be in a liquid form. The drug delivery mechanism of the first housing part 104 may be configured to engage with the drug cartridge 116 of the second housing part 106 to facilitate expulsion of the drug. The second housing part 106 may be detached from the first housing part 104 in order to insert a drug cartridge 116 or to remove a used cartridge. The first and second housing parts 104, 106 may be connected together in any suitable way, for example with a screw or bayonet type connection. The first and second housing parts 104, 106 may be non-reversibly connected together is such a way as the drug cartridge 116 is permanently contained with the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 is connected to an internal threading system which causes the dial 108 to be displaced axially from the housing 102 as it is rotated in a first direction. The device 100 is configured, once a drug dose has been set by rotation of the rotatable dial 108, to deliver the set drug dose when a user exerts an axial force at the proximal end of the device. In some injection pen devices, the rotatable dial 108 may support a button (not shown) which must be depressed in order to deliver the set drug dose.

Figure 2:
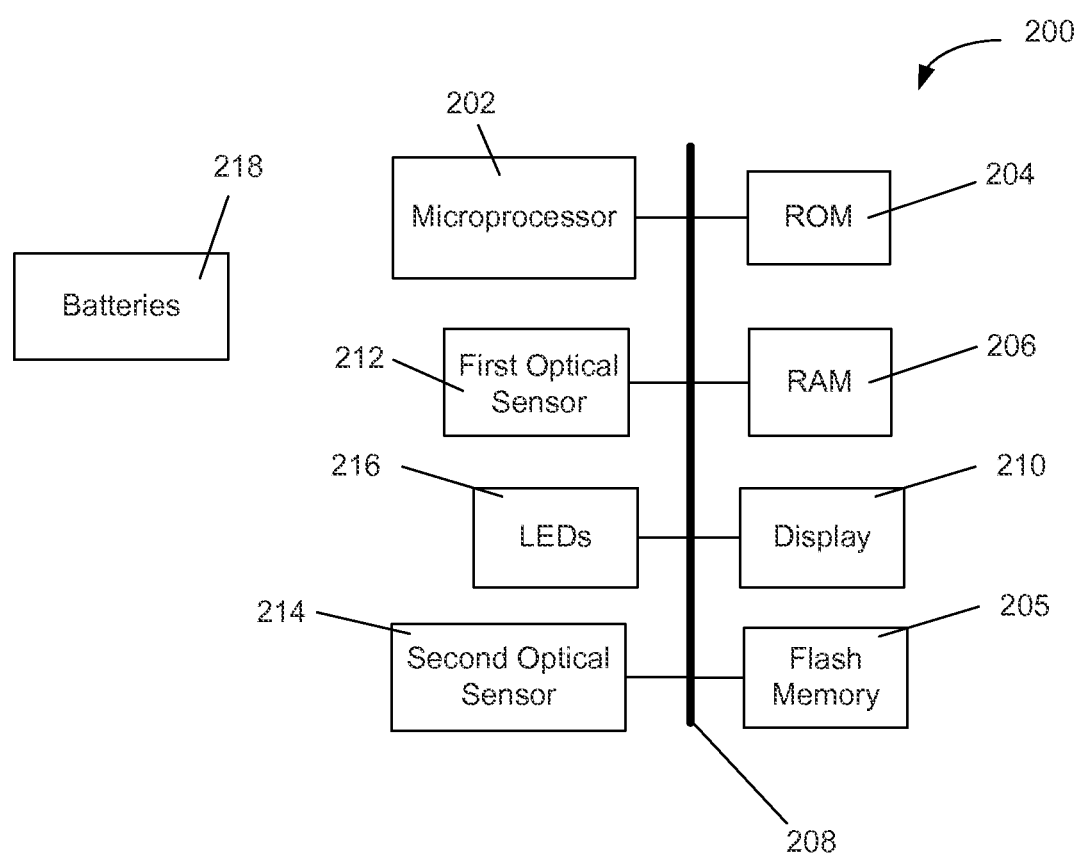
FIG. 2 shows a schematic diagram of some of the electronic components suitable for implementing the present invention.

Referring now to FIG. 2, a schematic diagram of electrical circuitry 200 suitable for implementing the present invention is shown. The circuitry 200 comprises a microprocessor 202, a non-volatile memory such as a ROM 204, a writable non-volatile memory such as flash memory 205, a volatile memory such as a RAM 206, a display 210, a first optical sensor 212, a second optical sensor 214, LEDs 216 and a bus 208 connecting each of these components. The circuitry 200 also comprises batteries 218 or some other suitable source of power for providing power to each of the components.

The circuitry 200 may be integral with the device 100. Alternatively, the circuitry 200 may be contained within an electronic module that can be attached to the device 100. In addition, the circuitry 200 may comprise additional sensors, such as an optical character recognition (OCR) system or acoustical sensors.

The ROM 204 may be configured to store software and/or firmware. This software/firmware may control operations of the microprocessor 202. The microprocessor 202 utilises RAM 206 to execute the software/firmware stored in the ROM to control operation of the display 210. As such the microprocessor 202 may also comprise a display driver. The processor 202 utilises the flash memory 205 to store determined amounts of dose dialed and/or determined amounts of dose dispensed, as will be described in more detail below.

The batteries 218 may provide power for each of the components including the first and second optical sensors 212, 214 and LEDs 216. The supply of power to the first and second optical sensors 212, 214 and LEDs 216 may be controlled by the microprocessor 202. The microprocessor 202 may receive signals from the first and second optical sensors 212, 214 and is configured to interpret these signals.

Information may be provided on the display 210 at suitable times by operation of the software/firmware and the microprocessor 202. This information may include measurements determined from the signals received by the microprocessor 202 from the first and second optical sensors 212, 214 such as the drug dose which has been set and/or delivered. The display 210 may also show additional information, such as the actual time, the time of the last usage/injection, a remaining battery capacity, one or more warning signs, and/or the like.

The first and second optical sensors 212, 214 may be configured to capture pixelated greyscale images of printed images or patterns which optically encode information. The images or patterns may be printed on movable parts of the drug delivery device 100 which the first and second optical sensors 212, 214 are configured to be directed at. The one or more LEDs 216 are also directed at the printed images/patterns in order to provide illumination for the sensors 212, 214. For example, the first and second optical sensors 212, 214 may detect the intensity pattern of light reflected from the printed images/patterns. The LEDs 216 and sensors 212, 214 may be configured to operate at various wavelengths of light. The LEDs 216 and sensors 212, 214 may, for example, operate in infra-red. Each of the first and second optical sensors 212, 214 may have an integral LED 216, or the LEDs 216 and sensors 212, 214 may comprise separate units. Software stored in the ROM 204 allows the microprocessor 202 to determine from the signals received from the first and second optical sensors 212, 214 whether first and second rotatable components are rotating. Software also allows the microprocessor 202 to analyse and decode images received from the first and second optical sensors 212, 214 and to determine a rotational position of each of the first and second rotatable components.

The circuitry 200 may comprise further components which are not shown. For example, the circuitry 200 may comprise one or more user inputs in the form of hardware or software keys. The circuitry 200 may comprise a speaker and/or a microphone. The circuitry 200 may also comprise one or more means of removing or communicating information stored in the ROM 204 or flash memory 205, such as a wireless transceiver, a card slot or a cable port (e.g. a USB port).

Figure 3:
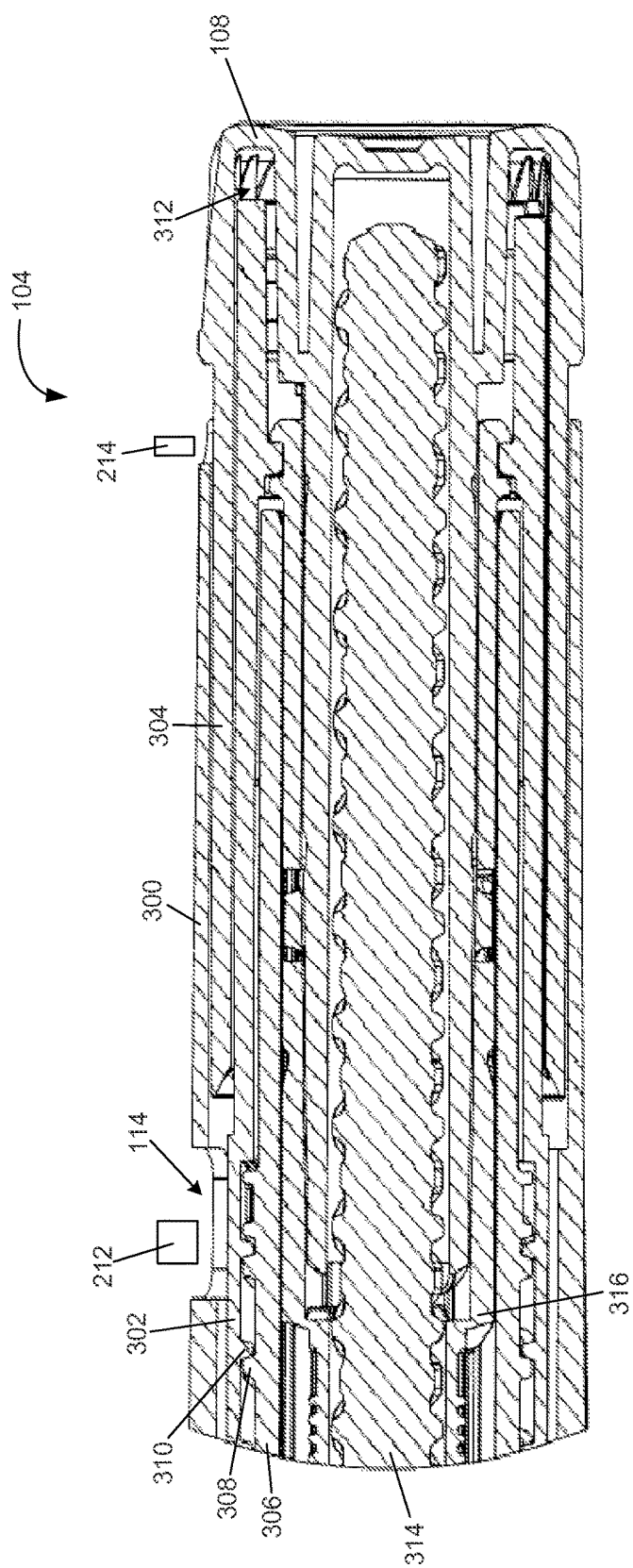
FIG. 3 is a cross-section showing detail of a dose setting mechanism of a drug delivery device according to embodiments of the invention.

FIG. 3 is a cross-sectional view of a part of a dose setting mechanism of a drug delivery device 100. A detailed example of the operation of a dose setting and delivery mechanism supported within the first housing part 104 can be found in published PCT application WO2010/139640, which is incorporated herein by reference. This document gives details of one particular drug delivery device mechanism. However, the invention may be implemented in a wide variety of different drug delivery devices having different mechanisms.

Referring now to FIG. 3, the first housing part 104 comprises an outer housing 300, an inner housing 306 and an encoded number sleeve 302. These components are hollow cylinders arranged concentrically. The encoded number sleeve 302 is disposed between the inner and outer housings 306, 300. The rotatable dial 108 is located at the proximal end of the outer housing 300. Integral with the rotatable dial 108 is a dialing sleeve 304. The dialing sleeve 304 comprises a hollow cylinder disposed between the outer housing 300 and the encoded number sleeve 302.

A recess 114 is provided in the outer housing 300. Electronic components including the display 210 may be received in the recess 114. The first optical sensor 212 (also referred to herein as the number sleeve sensor 212) is shown schematically at the position of the recess 114. The number sleeve sensor 212 may be part of the electronic module received in the recess 114, or alternatively may be part of an external device configured to be attached to the drug delivery device 100. The second optical sensor 214 (also referred to herein as the dialing sleeve sensor 214) is shown schematically disposed at the proximal end of the outer housing 300. The dialing sleeve sensor 214 may be an integral part of the drug delivery device 100. For example, the dialing sleeve sensor may be received in a secondary recess (not shown) or the outer housing 300. Alternatively, the dialing sleeve sensor 214 may be part of an external device configured to be attached to the drug delivery device 100. In either case, when in use the dialing sleeve sensor 214 is arranged to be directed at an outer surface of the dialing sleeve 304.

As can be seen in FIG. 3, the outer diameter of the encoded number sleeve 302 may be reduced towards the proximal end of the first housing part 104 in order to provide a space for the dialing sleeve 304. The thickness of the outer housing 300 may also be reduced at the proximal end to provide this space. The dialing sleeve 304 extends into the first housing part 104 no further than the recess 114 such that when the first optical sensor 212 is positioned at or in the recess 114 it is directed at the encoded number sleeve 302, while the second optical sensor 214 is directed at the dialing sleeve 304.

The inner housing 306 has a thread 308 provided on a part of its outer surface. The encoded number sleeve 302 has a corresponding thread disposed on a part of its inner surface. The inner housing 306 is fixed relative to the outer housing 300. Therefore the threaded engagement between the inner housing 306 and the number sleeve 302 causes the number sleeve to move axially relative to the outer housing 300 when rotated (and vice versa). In an initial configuration (shown in FIG. 3), the rotatable dial 108 is coupled to the encoded number sleeve 302. This coupling may be provided by a toothed engagement at the proximal end of the encoded number sleeve 302. However, the skilled person will be aware of other methods by which these components may be coupled. The dial 108 and the encoded number sleeve 302 may be coupled via a third rotatable component. Thus when the rotatable dial 108 is rotated, the encoded number sleeve 302 also rotates. This causes the rotatable dial 108 and all components coupled thereto to move axially out of the first housing part 104. If the dial 108 is rotated in the opposite direction, it moves back into the first housing part 104.

After a dose has been dialed into the drug delivery device 100 it may be dispensed by applying an axial load to the distal end of the rotatable dial 108. The rotatable dial 108 and integral dialing sleeve 304 are able to move axially relative to the encoded number sleeve 302 when this axial load is applied. Biasing means (not shown) may be provided to bias the rotatable dial 108 and the number sleeve 302 apart, i.e. to bias the rotatable dial 108 in the distal direction relative to the number sleeve 302. This position is shown in FIG. 3. When a force sufficient to overcome the bias is applied, the rotatable dial moves axially so that the proximal end of the number sleeve 302 enters the space 312 internal to the rotatable dial 108. This relative axial movement between the rotatable dial and the number sleeve 302 causes these components to be decoupled. For example, the toothed engagement at the proximal end of the encoded number sleeve 302 may be disengaged or a clutch formed by a different part of the mechanism may be disengaged.

When all of the allowed relative movement between the rotatable dial 108 and number sleeve 302 has occurred, the axial load on the rotatable dial 108 is transferred to other components of the mechanism. The axial force is transferred to a spindle 314, disposed centrally within the mechanism, via a drive sleeve 316 in order to cause expulsion of a medicament from the drug cartridge 116. The axial force is also transferred to the encoded number sleeve 302 which moves axially back into the first housing part 104. Due to the threaded connection of the encoded number sleeve 302 with the inner housing 306, the number sleeve rotates as it moves axially back into the first housing part 104. As the rotatable dial 108 and integral dialing sleeve 304 are decoupled from the number sleeve 302 and coupled, via the drive sleeve 316, to the inner housing 306, they do not rotate as they move axially back into the first housing part 104.

Figure 4:
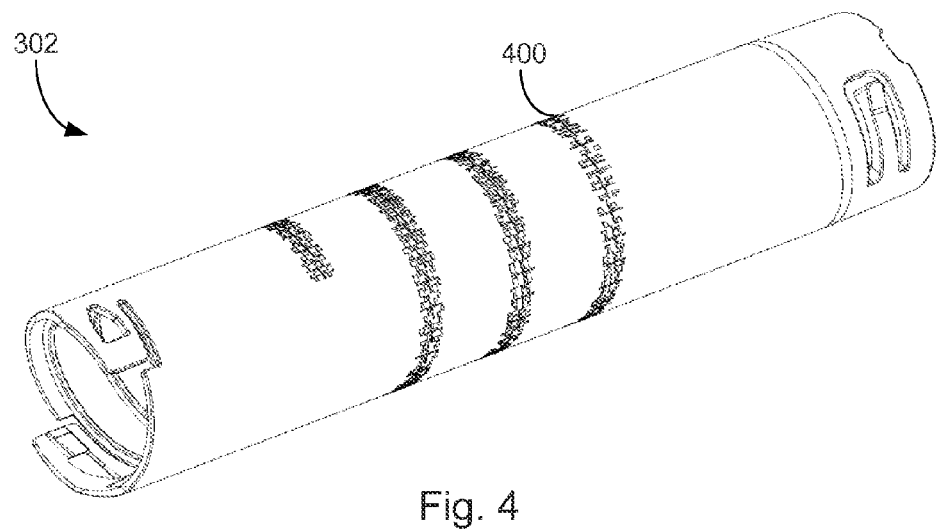
FIG. 4 shows an optically encoded sleeve suitable for use with the invention.
Figure 5:
FIG. 5 shows a 81 position optical code suitable for use with the invention.

FIG. 4 shows a perspective view of the encoded number sleeve 302 removed from the drug delivery device 100. The outer surface of the number sleeve 302 has a helical track 400 comprising a sequence of images. Each of the images encodes information and is designed to be viewed by the number sleeve sensor 212. The drug delivery device 100 may be configured to deliver a maximum of 80 units of medicament. The track 400 may therefore comprise a series of 81 encoded images encoding positions 0 to 80. FIG. 5 is a table showing an encoded image scheme which may be used in the present invention. Each of the images in this scheme is comprised of a number of data bits which may be coloured black or white. The images are repeated in the four quadrants of a square. This allows for the compensation of manufacturing tolerances which may prevent a single encoded image from being viewed fully by the number sleeve sensor 212. The scheme of FIG. 5 is merely one example of suitable encoded images. The encoded image scheme may instead comprise a series of dot matrix patterns, a series of barcodes or similar or standard Arabic numerals and may comprise a single image per position or multiple repeated images. The encoded images may be printed, marked, indented, etched or similar onto the track 400.

The encoded number sleeve 302 is arranged within the mechanism such that when no dose is dialed into the drug delivery device 100 the first encoded image (encoding position "0") is located directly underneath the recess 114. This allows the encoded image to be viewed by the first optical sensor 212. The pitch of the track 400 is the same as the threads on the encoded number sleeve 302 and inner housing 306 such that as the number sleeve 302 rotates and moves axially out of the first housing part 104 the track 400 remains located underneath the recess 114 in the outer housing 300. The first optical sensor 212 is configured to capture the images and to relay signals to the microprocessor 202. One or more LEDs 216 may illuminate the track 400 to allow the first optical sensor 212 to capture images. The microprocessor 202 is configured to employ software stored in the ROM 204 to determine the content of each image, for example which parts of the image are black and which parts are white, and to identify a corresponding rotational position of the encoded number sleeve 302 relative to the sensor 212. The microprocessor 202 may achieve this by consulting a table stored in the ROM 204 which relates the content of each image to a rotational position of the number sleeve 302 and hence to a drug dose which has been dialed.

Figure 6:
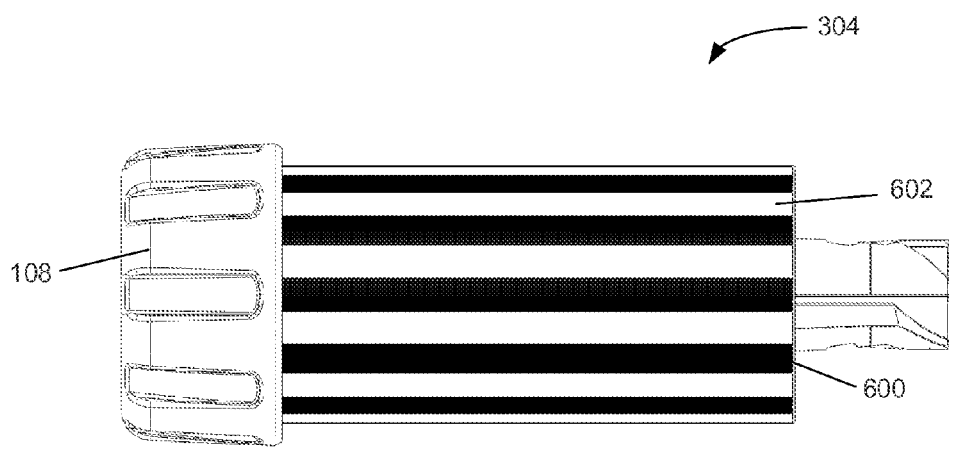
FIG. 6 shows an optically encoded dial suitable for use with the invention.

FIG. 6 is a plan view of the dialing sleeve 304 removed from the drug delivery device 100. The dialing sleeve 304 may be formed integrally with the rotatable dial 108, or maybe fixed to the rotatable dial 108. An incremental optical code is marked on an outer surface of the dialing sleeve 304. In the illustrated embodiment, the incremental code comprises alternating black bands 600 and white bands 602 extending axially. In some embodiments, the black bands 600 may be printed onto the dialing sleeve 304, which is white. In some other embodiments, the white bands 602 may also be printed. Any markings which allow rotation of the dialing sleeve 304 to be detected by the second optical sensor 214 may be used, such as a series of equally spaced marks. The surface of the dialing sleeve 304 may be a smooth cylinder, or may be corrugated. The corrugations may form the incremental markings. The dialing sleeve 304 may have a textured surface with well defined parameters allowing rotation of the dialing sleeve 304 to be detected.

Exemplary operation of the drug delivery device 100 will now be described. To dial a dose, a user grasps and twists the rotatable dial 108. The rotatable dial 108 is coupled to the encoded number sleeve 302, which therefore also rotates. The threaded connection between the encoded number sleeve 302 and the inner housing 306 causes the number sleeve 302 and dialing sleeve 304 to move axially out of the first housing part 104. The movement of the encoded number sleeve 302 and dialing sleeve 304 describes a helix.

As the number sleeve 302 moves helically, it is viewed by the first optical sensor 212. In some embodiments, the first optical sensor 212 is part of an electronics module received in the recess 114 in the outer housing 300. In other embodiments, the first optical sensor 212 is installed on the inner surface of the outer housing 300 during manufacture. The first optical sensor 212 may be connected to the other electronic components via conductive tracks running along and/or through the outer housing 300. In some other embodiments, the first optical sensor 212 is part of a supplemental device configured to be releasably attached to the drug delivery device 100. The first optical sensor 212 is configured to be directed at the encoded number sleeve 302 so as to view the encoded images of the track 400. One or more LEDs 216 are configured to illuminate the track 400. Images may be captured by the first optical sensor 212 at periodic intervals, for example twice per second. The images captured by the first optical sensor 212 are relayed to the microprocessor 202 for decoding.

As the dialing sleeve 304 moves helically, it is viewed by the second optical sensor 214. One or more LEDs 216 are configured to illuminate the surface of the dialing sleeve 304. The second optical sensor 214 observes alternating black and white stripes as the dialing sleeve 304 rotates. The second optical sensor 214 may capture images at predetermined intervals. The interval may be the same as or different to that of the first optical sensor 212. The images captured by the second optical sensor 214 are relayed to the microprocessor 202 for analysis. As the second optical sensor 214 is separated from the other electronics, conductive tracks may pass through the outer housing 300 or be printed onto an inner surface of the outer housing 300 to transmit signals to and from the sensor 214.

The angular width of the black and white bands 600, 602 is predetermined. For example, the surface of the dialing sleeve 304 may comprise 12 white bands 602 and 12 black bands 600. The microprocessor 202 can therefore use the received image signals to determine incrementally the amount of rotation (in either direction) of the dialing sleeve 304.

The field of view of each of the first and second optical sensors 212, 214 may be different. The field of view of the first optical sensor 212 must be large enough to encompass the whole of each encoded image in order for the image to be successfully decoded. The second optical sensor 214 only needs to determine whether the dialing sleeve 304 is rotating or not, so the field of view should preferably be no wider than the width of the black and white bands 600, 602.

Figure 7:
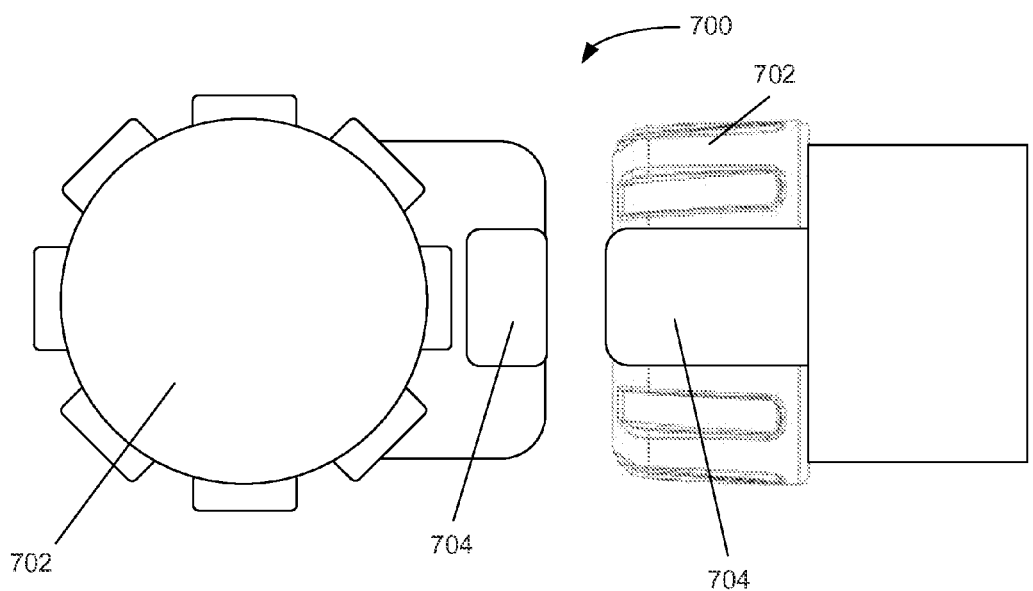
FIG. 7 shows the proximal end of a different drug delivery device in which the invention may be used.

As previously mentioned, the optical decoding system described herein is suitable for use with a wide range of different drug delivery devices. By way of further example, FIG. 7 shows the proximal end of a different drug delivery device 700 in which the invention may be used. FIG. 7 shows both an end view (left) and a plan view (right) of the proximal end of the drug delivery device 700.

The device 700 comprises the same first and second housing parts 104, 106, with the first housing part 104 containing the drug dose setting and delivery mechanism and the second housing part (not visible in FIG. 7) containing a drug cartridge. The device 700 also has a rotatable dial 702 (also referred to herein as a dose selector) similar or identical to that previously described.

The drug dose setting and delivery mechanism of the device 700 shown in FIG. 7 is constructed such that when the rotatable dial 702 is rotated to set a dose, it does not move axially out of the housing 104, but only rotates. This may be achieved by providing a drive spring which stores energy when the rotatable dial 702 is rotated. A cylindrical compression/tension or torsion spring is suitable for this purpose as it can be easily incorporated into the cylindrical body of the device 700.

After a dose has been dialed into the drug delivery device 700 it may be dispensed by applying an axial load to the distal end of the rotatable dial 702. The rotatable dial 702 may house a dose delivery button which is depressed in order to dispense a dose, or alternatively the whole rotatable dial 702 may be depressed axially in order to dispense a dose. The drug delivery device 700 also has a clutch mechanism which disengages the rotatable dial 702 from the drive spring when this axial load is applied allowing the drive spring to return to its original position without rotation of the rotatable dial 702. In returning to its original position, the drive spring forces a spindle to advance into the drug cartridge and thereby cause expulsion of a medicament from the drug cartridge.

In these embodiments, the encoded number sleeve (not visible in FIG. 7) is in mechanical communication with the drive spring and moves axially when energy is stored in or released from the drive spring. The encoded number sleeve moves in a first longitudinal direction when a dose is dialed into the drug delivery device 700 and in a second (opposite) longitudinal direction when a dose is dialed out of the drug delivery device 700 or when a dose is dispensed form the drug delivery device 700. The encoded number sleeve need not be a hollow cylinder as in the previously described embodiments, as it does not rotate, but only moves longitudinally. Thus the encoded images or numbers are printed in a longitudinal line on the encoded number sleeve such that they pass through the field of view of the first optical sensor 212.

In the embodiments represented by FIG. 7, the drug delivery device 700 also comprises a sensor arm 704 which extends from the first housing part 104 such that it is adjacent to the rotatable dial 702. The second optical sensor 214 is housed within this sensor arm 704 and directed at the rotatable dial 702. Alternatively, the sensor arm 704 and second optical sensor 214 may be part of an external device configured to be attached to the drug delivery device 100.

The second optical sensor 214 is configured to observe the rotation of the rotatable dial 702 directly. This removes the need to have a second window allowing the dialing sleeve to be visible to the second optical sensor 214 and the need for any modification of the dialing sleeve. The rotatable dial 702 has a corrugated surface to aid in gripping and turning the dial. The corrugations on the rotatable dial 702 may be coloured or shaded to allow the second optical sensor 214 to detect rotation of the dial 702. The angular width of the corrugations may be known, such that the amount of rotation can also be determined form the signals produced by the second optical sensor 214. However, in most embodiments it is only required that the second optical sensor 214 detect whether the rotatable dial 702 is rotating or stationary. Alternatively, the second optical sensor 214 may be replaced by another type of sensor, for example a proximity sensor which detects the changes in surface height of the dial 702 or a capacitive or hall sensor.

In use, a user grasps and twists the rotatable dial 702 to set a dose. The rotatable dial 702 rotates, but does not move axially. The rotatable dial 702 is coupled to a drive spring which stores energy as the dial is rotated. This in turn also causes the encoded number sleeve to move in a first longitudinal direction. As the number sleeve moves longitudinally, it is viewed by the first optical sensor 212. In some embodiments, the first optical sensor 212 is part of an electronics module received in the recess 114 in the first housing part 104. In other embodiments, the first optical sensor 212 is installed on the inner surface of the first housing part 104 during manufacture. The first optical sensor 212 may be connected to the other electronic components via conductive tracks running along and/or through the housing. In some other embodiments, the first optical sensor 212 is part of a supplemental device configured to be releasably attached to the drug delivery device 700.

As the rotatable dial 702 moves longitudinally, it is viewed by the second optical sensor 214. One or more LEDs 216 may be provided and configured to illuminate the surface of the rotatable dial 702. Alternatively, the second optical sensor 214 may rely on ambient light or may be another type of sensor as previously described. In some embodiments, the corrugations of the rotatable dial 702 form alternating black and white bands. The second optical sensor 214 observes these alternating black and white bands as the rotatable dial 702 rotates. The second optical sensor 214 may capture images at predetermined intervals. The interval may be the same as or different to that of the first optical sensor 212. The images captured by the second optical sensor 214 are relayed to the microprocessor 202 for analysis. Conductive tracks may pass through the housing or be printed onto an inner surface of the housing to transmit signals to and from the sensor 214.

The processor 202 receives signals from the first and second sensors 212, 214 and determines whether the drug delivery device 700 is in a drug dose dialing mode or a drug dose delivery mode. The processor may use the signals from the sensor to distinguish three different situations.

1) If the first optical sensor 212 detects movement of the number sleeve in a first longitudinal direction (e.g. towards the rotatable dial) and the second optical sensor 214 detects rotation of the rotatable dial 702, then the processor 202 determines that the drug delivery device 700 is in a drug dose dialing mode and that a dose is being dialed into the device.

2) If the first optical sensor 212 detects movement of the number sleeve in a second (opposite) longitudinal direction (e.g. towards the needle) and the second optical sensor 214 detects rotation of the rotatable dial 702, then the processor 202 determines that the drug delivery device 700 is in a drug dose dialing mode and that a dose is being dialed out of the device. This could be for example a situation, wherein a user corrects a too high dose that has been dialed into the device.

Another example could be that a user has decided to postpone application of the medicament and therefore is dialing out the previously dialed dose.

3) If the first optical sensor 212 detects movement of the number sleeve in a second (opposite) longitudinal direction (e.g. towards the needle) and the second optical sensor 214 detects that the rotatable dial 702 is not rotating, then the processor 202 determines that the drug delivery device 700 is in a drug dose delivery mode and that a dose is being ejected from the device.

Figure 8:
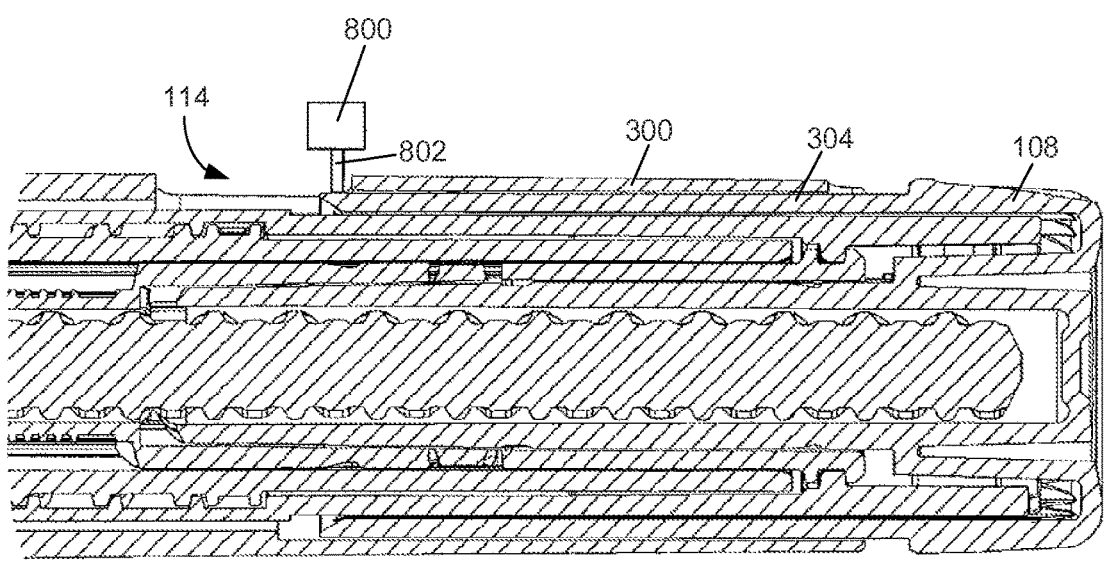
FIG. 8 is a cross-section through the dose setting mechanism of a drug delivery device showing an additional switch.

Referring also to FIG. 8, an activation switch 800 is shown. Although this feature is described with reference to the first type of drug delivery device 100, it is equally applicable to the second type of drug delivery device 700 described with reference to FIG. 7. The first and second optical sensors 212, 214 and LEDs 216 may be activated by rotation of the dial 108. This may be achieved by a switch 800 which is triggered whenever the dial 108 is rotated away from the zero dose position. The switch 800 may be comprised of an electromechanical switch having a protrusion 802. The protrusion 802 may be biased towards a protruding position. The protrusion 802 passes through a recess in the outer body 300, which may be part of the recess 114. The proximal end of the dialing sleeve 304 may be configured to contact the protrusion 802 when the drug delivery device 100 is in the zero dose position, as shown in FIG. 8. As the dial 108 is rotated away from the zero dose position, the dialing sleeve 304 moves axially. The protrusion 802 can then enter the space left by the dialing sleeve 304. This movement changes the state of the switch 800. In an alternative embodiment, the protrusion 802 may contact the outer surface of the encoded number sleeve 302. A recess may be cut into the outer surface of the encoded number sleeve 302 and the protrusion enters this recess when the sleeve 302 is in the zero dose position. The recess and/or the protrusion 802 may have sloped edges to allow the protrusion 802 to slide out of the recess when the sleeve 302 is rotated.

The state change of the switch 800 may be used as the trigger to activate the first and second optical sensors 212, 214 and LEDs 216. The drug delivery device 100 (or supplemental device in some embodiments) may remain in a standby or sleep mode until the switch 800 changes state. The first and second optical sensors 212, 214 and LEDs 216 are components which consume power while active. Optical sensors may also have relatively high standby current requirements. The drug delivery device 100 (or supplemental device in some embodiments) is portable and the batteries 218 have a limited capacity. The battery life of the drug delivery device 100 is therefore conserved by activating these components only at the required time. The first and second optical sensors 212, 214 and LEDs 216 may be deactivated when the drug delivery device 100 is returned to the zero dose position, or after a predetermined time delay after the delivery device 100 is returned to the zero dose position.

Referring again to the first described drug delivery device 100, software stored in the ROM 204 also allows the microprocessor 202 to use the signals received from the first and second optical sensors 212, 214 to determine a mode of operation of the drug delivery device 100. When the drug delivery device 100 is in a "dialing mode", the dial 108 is rotated to dial a dose into or out of the device 100. This causes both the encoded number sleeve 302 and dialing sleeve 304 to move helically, as previously described. The first optical sensor 212 views the encoded images on the track 400 passing in sequence. Each of these images encodes a unique rotational position, allowing the currently dialed dose to be determined. The second optical sensor 214 views the alternating black and white bands 600, 602 as they rotate past. As both sensors view helical motion, it is determined that the drug delivery device 100 is in a dialing mode. While the drug delivery device 100 is in the dialing mode, the output from the number sleeve sensor 212 can be used by the microprocessor to determine the value of the current dialed dose. This value can be displayed on the display 210.

When an axial load is applied to the rotatable dial 108, the drug delivery device 100 is in a "dispensing mode". The rotatable dial 108 and dialing sleeve 304 are de-coupled from the encoded number sleeve 302, as previously described. As the encoded number sleeve 302 translates back into the first housing part 104, it moves in the same helical way as in the dialing mode. However, the rotatable dial 108 and dialing sleeve 304 translate only and do not rotate. Therefore, during dispensing, the first optical sensor 212 views the encoded images on the track 400 passing in sequence, but the second optical sensor 214 views no change in the incremental encoded images on the dialing sleeve 304 and no change in the output of the second optical sensor 214 results. The microprocessor 202 can thus determine that the drug delivery device 100 is in a dispensing mode. While the drug delivery device 100 is in the dispensing mode, the output from the number sleeve sensor 212 can be used by the microprocessor to determine the value of an injected dose. This value can be displayed on the display 210 and stored in the flash memory 205. Results of previous dispensing action may be later recalled from the flash memory 205 and displayed on the display 210.

Being able to determine the mode of operation of the drug delivery device 100 is advantageous, as the drug delivery device 100 (or the attached supplemental device) is able to calculate electronically the dose of medicament which has been delivered. For example, a user may dial in a dose but then dial some of the dose out before dispensing the remaining dose. Alternatively, a user may deliver only a part of a dose and may dial the remaining dose out. It is important to accurately record the dose of medicament which has actually been delivered in order to accurately assess the effect of the medicament on the user's health and for the calculation of future medicament doses.

The invention claimed is:

1. A drug delivery device comprising:
a processor;
a first rotatable component and a second rotatable component;
a first optical sensor directed at the first rotatable component;
a second optical sensor directed at the second rotatable component; and
a computer-readable medium storing instructions that, when executed by the processor, cause the drug delivery device to perform functions comprising:
receiving a first signal from the first optical sensor, wherein the first signal indicates whether the first rotatable component is rotating or not;
receiving a second signal from the second optical sensor, wherein the second signal indicates whether the second rotatable component is rotating or not; and
using the first signal and the second signal to determine whether the drug delivery device is in a drug dose selection mode or a drug dose delivery mode.

2. The drug delivery device according to claim 1, wherein the first signal also represents a dosage value encoded on the first rotatable component, the functions further comprising using the first signal to determine a drug dose that has been delivered and to cause a record of the delivered dose to be stored in a memory.

3. The drug delivery device according to claim 2, wherein the drug delivery device further comprises a display device and wherein the functions further comprise causing the display device to display an indication of the drug dose that has been delivered.

4. The drug delivery device according to claim 1, wherein the drug delivery device further comprises one or more LEDs configured to illuminate portions of the first rotatable component or the second rotatable component.

5. The drug delivery device according to claim 1, wherein the drug delivery device further comprises a switch and wherein a change in the state of the switch is configured to cause the first optical sensor and the second optical sensor to be activated.

6. The drug delivery device according to claim 5, wherein the drug delivery device and the switch are configured such that the state of the switch changes when the drug delivery device moves from a zero unit drug dose arrangement to a single unit drug dose arrangement.

7. The drug delivery device according to claim 1, wherein:
the first rotatable component is arranged to rotate and translate relative to the first optical sensor when the drug delivery device is in the drug dose selection mode and when the drug delivery device is in the drug dose delivery mode; and
the second rotatable component is arranged to rotate and translate relative to the second optical sensor when the drug delivery device is in the drug dose selection mode and only to translate relative to the second optical sensor when the drug delivery device is in the drug dose delivery mode.

8. The drug delivery device according to claim 1, wherein:
the first rotatable component is arranged to translate relative to the first optical sensor when the drug delivery device is in the drug dose selection mode and when the drug delivery device is in the drug dose delivery mode; and
the second rotatable component is arranged to rotate relative to the second optical sensor when the drug delivery device is in the drug dose selection mode and to remain stationary when the drug delivery device is in the drug dose delivery mode.

9. A method of determining a mode of operation of a drug delivery device, the method comprising:
receiving a first signal from a first optical sensor directed at a first rotatable component of the drug delivery device, wherein the first signal indicates whether the first rotatable component is rotating or not;
receiving a second signal from a second optical sensor directed at a second rotatable component of the drug delivery device, wherein the second signal indicates whether the second rotatable component is rotating or not; and
using the first signal and the second signal to determine whether the drug delivery device is in a drug dose selection mode or a drug dose delivery mode.

* * * * *